United States Patent [19]
Ohyama et al.

[11] Patent Number: 6,146,853
[45] Date of Patent: Nov. 14, 2000

[54] CYCLIC DEPSIPEPTIDE PF 1022G

[75] Inventors: Makoto Ohyama; Masaaki Takahashi; Yoshiya Shigematsu; Osamu Sakanaka; Yashushi Murai; Katsuharau Iinuma, all of Odawara, Japan

[73] Assignee: Meiji Seika Kaisha Ltd., Tokyo, Japan

[21] Appl. No.: 09/505,294

[22] Filed: Feb. 16, 2000

Related U.S. Application Data

[62] Division of application No. 09/242,041, filed as application No. PCT/JP97/02772, Aug. 7, 1997, Pat. No. 6,043,058.

[30]    Foreign Application Priority Data

Aug. 7, 1996 [JP] Japan ..................... 8-208201

[51] Int. Cl.[7] .......................... A61K 38/12; C07K 16/00; C12P 21/04
[52] U.S. Cl. .................. 435/71.1; 530/317; 530/323; 530/328; 514/9; 514/11
[58] Field of Search ..................... 530/323, 300, 530/317, 328; 930/270; 435/71.1; 514/9, 11

[56]    References Cited

U.S. PATENT DOCUMENTS 5,116,815  5/1992  Takagi et al. .
5,747,448  5/1998  Ohyama et al. .

OTHER PUBLICATIONS

Sasaki, T. et al., A New Anthelmintic Cyclodepsipeptide, PF 1022A, The Journal of Antibiotics, vol. 45, No. 5, pp. 692–697.

*Primary Examiner*—Leon B. Lankford, Jr.
*Assistant Examiner*—Michele Flood
*Attorney, Agent, or Firm*—Larson & Taylor

[57]    ABSTRACT

Known cyclic depsipeptides which are PF 1022F substance and PF 1022H substance, as well as a novel cyclic depsipeptide, PF 1022G substance, are now prepared simultaneously by cultivating a fungal strain capable of producing PF 1022F substance, PF 1022G substance and PF 1022H substance represented by the known PF 1022 strain (deposited under FERM BP-2671) which is a kind of fungus belonging to asporous imperfect fungi (the order Agonomycetales) and is presumable to belong to the genus Xylaria or the genus Rosellinia in the family Xylariaceae. The PF 1022G substance has the formula:

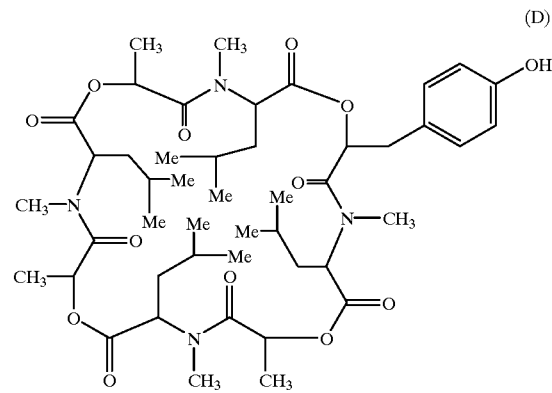

(D)

1 Claim, 3 Drawing Sheets

CYCLIC DEPSIPEPTIDE PF 1022G

This application is a divisional of application No. 09/242,041, Feb. 5, 1999 of U.S. Pat. No. 6,043,058, Mar. 28, 2000 which is a 371 of PCT JP 97/02772, Aug. 7, 1997.

TECHNICAL FIELD

This invention relates to a fermentative process for the preparation of PF 1022F substance and PF 1022H substance which are known cyclic depsipeptides, and for the preparation of PF 1022G substance which is a novel depsipeptide. This invention further relates to PF 1022G substance as the novel depsipeptide.

BACKGROUND ART

Hitherto, there are known a number of compounds possessing an anthelmintic activity. Among such compounds, destomycin A, hygromycin B, avermectin and others may be exemplified as such known compounds which are products of microorganisms and which have an anthelmintic activity, but they are of a very small minority among the known anthelmintically active compounds. Takagi et al. made investigations earlier to search for the substances having an anthelmintic activity against roundworms living in domestic fowls, and as a result they discovered PF 1022 substance (which may also be called as PF 1022A substance) as a product of a microorganism, and PF 1022 substance is classified under cyclic depsipeptides having an anthelmintic activity (refer to Japanese Patent Application First Publication Kokai Hei 3-35796, Japanese Patent No.2608479, U.S. Pat. No. 5,116,815 and European Patent Application First Publication No. 0382173A2). This PF 1022 substance is the cyclic depsipeptide represented by the following formula (A):

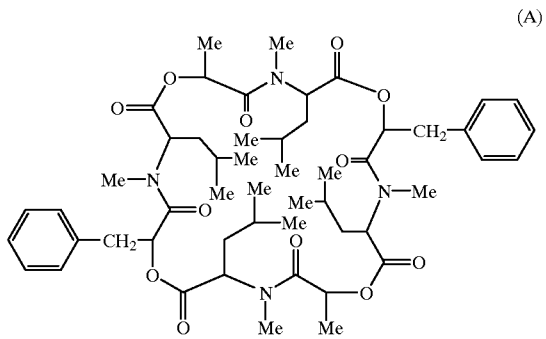

wherein Me stands for methyl group Me has the same meaning in the following descriptions given hereinafter.

PF 1022 substance is a cyclic depsipeptide constituted by L-N-methylleucine [(CH$_3$)$_2$CHCH$_2$CH(NHCH$_3$)COOH] (Code: H-L-MeLeu-OH), D-lactic acid [CH$_3$CH(OH)-COOH] (Code: H-D-Lac-OH) and D-phenyllactic acid [C$_6$H$_5$CH$_2$CH(OH)COOH] (Code: H-D-PhLac-OH), which are bonded with each other through ester- and amido-bonds. PF 1022 substance may also be represented by the following formula (B).

Formula (B):

Cyclo(L-MeLeu-D-Lac-L-MeLeu-D-PhLac-L-MeLeu-D-Lac-L-MeLeu-D-PhLac) (B)

The present inventors further discovered PF 1022B substance, PF 1022C substance and PF 1022D substance as the products of the microorganism, and these substances are PF 1022-related compounds having an anthelmintic activity (refer to Japanese Patent Application First Publication Kokai Hei 5-170749). Further, PF 1022E substance was found as a product of the microorganism (refer to Japanese Patent Application First Publication Kokai Hei 6-184126). The microorganism used here is PF 1022 strain hereinafter described. The structural formulae of PF 1022B to E substances are given in Internationally published specification WO94/19334 (published on 1st September, 1994) of PCT Application PCT/JP94/00252, and in European Patent Application First-published specification No. 0685469A1.

A series of cyclic depsipeptide derivatives which are produced through chemical synthetic processes by the present inventors, as well as some processes for their preparation are described in Japanese Patent Application First Publication Kokai Hei 5-320148 and Japanese Patent Application First Publication Kokai Hei 6-340694 and also in PCT Internationally published specification WO94/19334 mentioned above. Yet further, another series of cyclic depsipeptides prepared by chemical synthesis by Nishiyama et al. and their preparation methods are given in Japanese Patent Application First Publication Kokai Hei 5-229997, Internationally published specification WO93/19053 of PCT Application PCT/JP93/00286, U.S. Pat. No. 5,514,773 and Internationally published specification WO95/07272 of PCT Application PCT/JP94/01446.

In addition, Examples 3 and 8 of the above PCT Internationally published specification WO94/19334 describe PF 1022-002 substance and PF 1022-202 substance, respectively, which were chemically synthesized by the present inventors. PF 1022-002 substance is reported in another name of PF 1022F substance and PF 1022-202 substance is reported in another name of PF 1022H substance in PCT Internationally published specification WO97/11064 (published on Mar. 27, 1997) of PCT Application PCT/JP96/02730(with International filing date: Sep. 20, 1996). The PCT Application PCT/JP96/02730 was filed with claiming a priority from Japanese Patent Application Hei 7-244051 filed on Sep. 22, 1995 and is claiming a series of such novel derivatives of PF 1022 substance which are recently synthesized by the present inventors.

Incidentally, in PCT Internationally published specification WO 97/20945 (published on Jun. 12, 1997) of PCT Application PCT/EP96/05190 (International filing date: Nov. 25, 1996), Jeschke et al. have proposed a process for the preparation of cyclodepsipeptides comprising aryllactic acid as one constituent of the cyclodepsipeptide, which process comprises converting an amino acid such as 4-nitrophenylalanine or a 2-hydroxy carboxylic acid such as 4-nitrophenyllactic acid in the presence of a microbial strain (deposited as DSM 10345) of *Mycellia sterilia* (which is a generic name of conidium-unformable fungi) or in the presence of an enzyme extracted from said microbial strain.

It is generally known that such diseases called as parasitic diseases can bring about serious damages not only to the health of mankind and animals but also to useful vegetations cultivated in the agriculture. In view of this, there always exist earnest demands for providing some novel and useful substances having an anthelmintic activity, and also for providing some processes capable of producing such novel substances advantageously.

Taking the above-mentioned demands into due consideration, we, the present inventors, had proceeded a series of our investigation earlier, and on the basis of the investigation we already succeeded in providing a new fermentative process for the preparation and a new chemically synthetic process for the preparation of a series of the above-mentioned known or novel cyclic depsipeptides and their derivatives which possess an anthelmintic activity and are therefore useful as therapeutic and preventive medicines for the parasitic diseases.

The above-mentioned PF 1022H substance is a cyclic depsipeptide obtained through a chemical synthesis by the present inventors, and we have further found that this PF 1022H substance is also useful as a starting material for the preparation of a series of depsipeptide derivatives possessing an improved anthelmintic activity, if the functional group or groups of PF 1022H substance is or are chemically modified further.

As measures for preparing the cyclic depsipeptides having such a complex cyclic skeleton as seen in the structural formula (A) above, there are two routes, namely a route by chemical synthesis and another route by cultivation of a microorganism. The fermentative process for preparing the cyclic depsipeptides by cultivation of microorganism shall leave the production of the intended substances of the complex structure to the actions of the microorganism used. In comparison with the chemically synthetic process, the fermentative process is generally advantageous in practice, in respect of the overall period of time required, labors and expenses and other points, and the fermentative process may be operated in a easier and more convenient way.

For the several reasons above-mentioned, the PF 1022F substance and PF 1022H substance are requested to be prepared in a more convenient way by the cultivation of microorganism rather than by the chemical synthetic route. It is also requested that such novel cyclic depsipeptides which have not yet been disclosed in literature are prepared through such convenient, fermentative process by the cultivation of a microorganism, because such novel cyclic depsipeptides will have such possibilities that they possess an anthelmintic activity or some other pharmaceutically useful activities, and that they are utilizable as intermediate materials for chemically synthesizing some other derivatives possessing some useful activities.

One of the objects of this invention is, therefore, to provide a novel process for the preparation of the PF 1022F substance and PF 1022H substance by the cultivation of a microorganism. Another object of this invention is to provide novel, useful cyclic depsipeptides by the cultivation of a microorganism.

DISCLOSURE OF THE INVENTION

In order to achieve the above-mentioned objects, we have carried out cultivation of a variety of microorganisms and have made studies on the metabolite products so obtained of these microorganisms. As a part of these studies, we further have made detailed investigations on the substances as produced in the culture broth of the filamentous fungus, PF 1022 strain (deposited as FERM BP-2671 under Budapest Treaty), which strain was judged to belong to the order Agonomycetales and which was previously used in the fermentative process for preparation of PF 1022A substance of formula (A) shown above (refer to Japanese Patent No.2608479 and U.S. Pat. No. 5,116,815) and also in the fermentative process for preparation of PF 1022B, C, D and E substances. As a result, we have now found that the PF 1022F substance and PF 1022H substance are simultaneously produced and accumulated in the said culture broth of the PF 1022 strain.

We have further discovered that a novel cyclic depsipeptide is also produced in the same culture broth of the PF 1022 strain, and we have designated this novel substance as PF 1022G substance. Also, we have succeeded in recovering the PF 1022F substance, PF 1022H substance and PF 1022G substance from the resultant culture of the PF 1022 strain and then purifying and isolating these substances, respectively. Further, we have examined physico-chemical properties of PF 1022G substance, and we have determined the chemical structural formula thereof and thus confirmed PF 1022G substance to be a novel cyclic depsipeptide.

PF 1022F substance is a cyclic depsipeptide represented by the following formula (B):

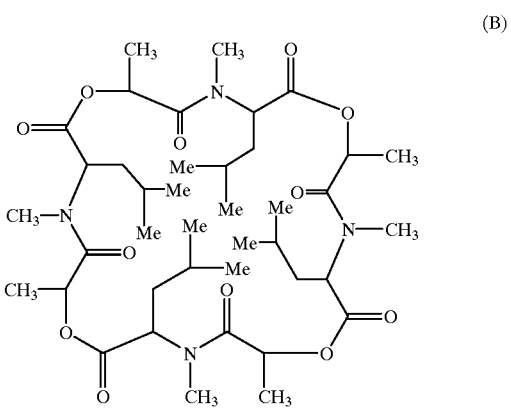

wherein Me stands for methyl group and Me has the same meaning in the following descriptions given hereinafter.

PF 1022H substance is a cyclic depsipeptide represented by the following formula (C):

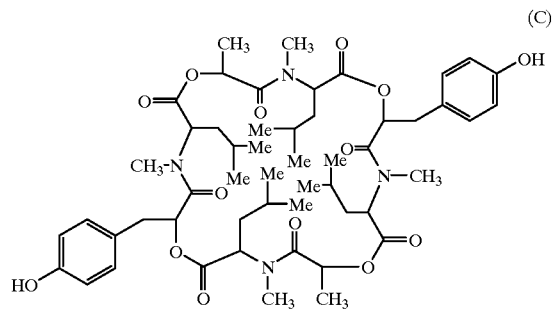

The novel PF 1022G substance now obtained by the present inventors is a cyclic depsipeptide represented by the following formula (D):

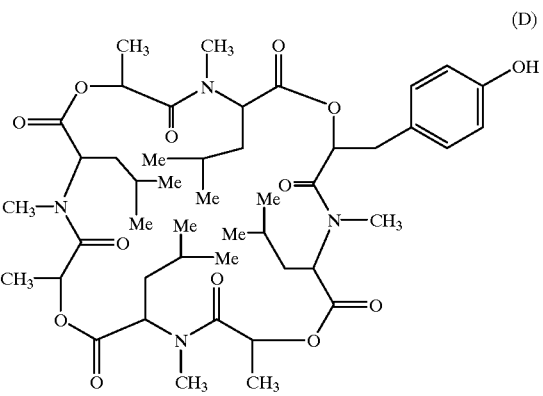

We have further studied on taxonomic distinction of the PF 1022 strain (deposited under FERM BP-2671) above-mentioned, but we could not yet specified completely the taxonomic position of the PF 1022 strain, because the PF 1022 strain is such a fungus which does not cause any conidium formation. According to our systemic analysis for analyzing the base-sequence of 18S rDNA of the PF 1022 strain, however, PF 1022 strain is considered surely to belong to the family Xylariaceae and now is presumed to be close to the genus Xylaria or the genus Rosellinia falling under this Xylariaceal family.

In this invention, therefore, PF 1022 strain is regarded presumably or tentatively to be a strain belonging to the genus Xylaria or the genus Rosellinia.

According to a first aspect of this invention, therefore, there is provided a process for the preparation of PF 1022F substance, PF 1022G substance and PF 1022H substance, which are represented by the following general formula (I)

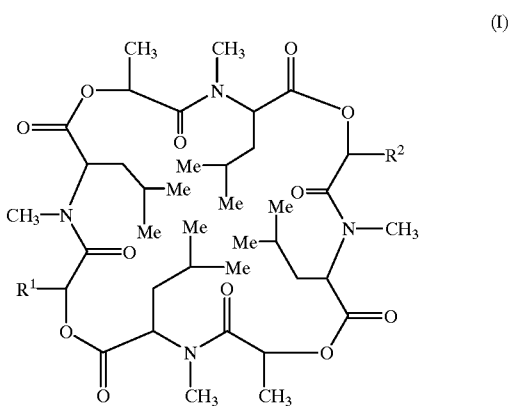

(I)

wherein both of R¹ and R² each denote methyl group for PF 1022F substance, but R¹ denotes methyl group and R² denotes p-hydroxybenzyl group for PF 1022G substance, and both of R¹ and R² each denote p-hydroxybenzyl group for PF 1022H substance, which process comprises cultivating a fungal strain capable of producing PF 1022F substance, PF 1022G substance and PF 1022H substance and belonging to the genus Xylaria or the genus Rosellinia, in a culture medium containing carbon and nitrogen sources, thereby producing and accumulating PF 1022F substance, PF 1022G substance and PF 1022H substance in the resulting culture, recovering PF 1022F substance, PF 1022G substance and PF 1022H substance from the said culture and then isolating PF 1022F substance, PF 1022G substance and PF 1022H substance separately from each other.

The fungal strain capable of producing PF 1022F substance, PF 1022G substance and PF 1022H substance, which is to be used in the process of the first aspect of this invention, may be any of those strains which are capable of producing PF 1022F substance, PF 1022G substance and PF 1022H substance, as long as it belongs to the genus Xylaria or the genus Rosellinia of the family Xylariaceae. One preferred example of the fungal strains capable of producing PF 1022F substance, PF 1022G substance and PF 1022H substance is the aforesaid PF 1022 strain which is an asporous imperfect fungus and which was isolated from a vegetative sample collected in Ibaraki Prefecture, Japan.

The PF 1022 strain has been deposited at National Institute of Bioscience and Human-Technology, Agency of Industrial Science & Technology (located at No.1-3, 1-chome, Higashi, Tsukuba-shi, Ibaraki Prefecture, Japan) since Jan. 24, 1989 under the access number FERM P-10504, and then since Dec. 4, 1989 under the access number FERM BP-2671 in terms of the Budapest Treaty.

Micological properties of the PF 1022 strain are described in detail in the specification of Japanese Patent Application Kokai No. Hei 3-35796, the specification of U.S. Pat. No. 5,116,815 and the Journal of Antibiotics, Vol.45, page 692~ (1992).

Like the other asporous imperfect fungal strains (the order Agonomycetales), the PF 1022 strain is labile in its properties. Thus, for example, the PF 1022 strain itself, or any mutant as derived from this strain, phenotypic conjugation (spontaneously generated or artificially induced), or genetic recombinant of said strain may be used in practicing the process of this invention, if it can produce the PF 1022F substance, PF 1022G substance and PF 1022H substance.

In the process according to the first aspect of this invention, a fungal strain capable of producing PF 1022F substance, PF 1022G substance and PF 1022H substance is cultivated according to the following cultivation procedure.

Thus, in the process according to the first aspect of this invention, the above-mentioned PF 1022F substance, PF 1022G substance and PF 1022H substance-producing strain is cultivated in a culture medium containing such ordinary carbon source and nitrogen source which can be generally utilized as nutrients by ordinary Microorganisms. As such nutrients, there may be used those nutrients which are known to have been utilized for the cultivation of fungi. For example, as the carbon sources are usable the ordinarily utilized carbon sources such as glucose, sucrose, starch syrup, dextrin, starch, glycerol, molasses, animal oils, vegetable oils, and the like. Usable as the nitrogen sources are the ordinarily utilized nitrogen sources such as soybean flour, wheat germ, corn steep liquor, cotton seed oil, meat extract, peptone, yeast extract, ammonium sulfate, sodium nitrate, urea, and the like. Inorganic salts capable of producing potassium, calcium, magnesium, cobalt, chloride, phosphate, sulfate and other ions may effectively be added to the culture medium, as necessary. Furthermore, organic and inorganic substances capable of promoting the growth of the fungal strain and thus promoting the production of PF 1022F substance, PF 1022G substance and PF 1022H substance may also be added in an appropriate amount.

For the methods of the cultivation of said strain, a cultivation method carried out under aerobic conditions is suitable, and particularly the cultivation method under submerged conditions is most suitable. The temperature range of 15~30° C. is suitable for the cultivation, but optimally the cultivation may be effected at a temperature of about 26° C. in most instances. In shake-cultivation or tank-cultivation, the production of PF 1022F substance, PF 1022G substance and PF 1022H substance will usually arrive at a maximum accumulation of these substances in 2 to 10 days, although the incubation period required therefor may vary depending upon the composition of the culture medium and the cultivation conditions employed. When the accumulation of PF 1022F substance, PF 1022G substance and PF 1022H substance has arrived at their peak, the cultivation step is discontinued. The resulting culture is then separated by filtration or by a centrifugal operation to give solid portion including the cultured cells and other solid materials and to give the broth filtrate. The filtration operation may be effected using a filtering aid such as diatomaceous earth, etc.

The recovery of PF 1022F substance, PF 1022G substance and PF 1022H substance as produced by the above cultivation of the microbial strain may be effected in the following manner. Thus, the recovery of PF 1022F substance, PF 1022G substance and PF 1022H substance from the resultant culture may generally be carried out by ordinary procedure of separation with utilizing its physico-chemical characteristics, for example, by solvent extraction or adsorption, ion-exchange resin treatment, partition column chromatography, gel filtration, dialysis, precipitation and so on, either alone or in an appropriate combination.

Since PF 1022F substance, PF 1022G substance and PF 1022H substance are insoluble in water, these substances exist mainly in the cultured cells rather than in the broth filtrate. Thus, to be concrete, PF 1022F, G and H substances may be extracted from the cultured cells with an organic solvent or an aqueous organic solvent, for example, methanol or ethyl acetate, or acetone-water, acetonitrile-water, etc. Further, in order to isolate PF 1022F substance, PF 1022G substance and PF 1022H substance from each other and then to purify each of them, there may be utilized a chromatographic method with silica gel (e.g. Wako gel C-200, produced by Wako Junyaku K.K.), alumina, or the like as an adsorbent, or a chromatographic method with a gel filtration agent such as Sephadex LH-20 (a product of Pharmacia Co.), Toyopal HW-40 (a product of Toso Co., Ltd.). For further purification, crystallization of each of PF 1022 F substance, PF 1022G substance or PF 1022H substance may be effected from a single solvent (e.g. methanol, ethyl acetate, etc.) or a mixed solvent (e.g. methanol-water, ethyl acetate-n-hexane, diethylether-n-hexane, etc.).

By adopting such isolation and purification processes as above-mentioned, either alone or in any appropriate combination thereof, PF 1022F substance, PF 1022G substance and PF 1022H substance may be obtained separately from each other at a high purity.

By the way, it is desirable that the process according to the first aspect of this invention includes the steps of separating from the resulting culture the cultured cells of the strain capable of producing PF 1022F substance, PF 1022G substance and PF 1022H substance, extracting the cultured cells so separated with an organic solvent or an aqueous organic solvent to obtain an extract containing PF 1022F substance, PF 1022G substance and PF 1022H substance, concentrating said extract to allow crystals comprising PF 1022G substance and PF 1022H substance to precipitate therein, filtering the resulting concentrated solution to separate said crystals and the filtrate containing PF 1022F substance, and isolating PF 1022G substance and PF 1022H substance, respectively, from the crystals, and also isolating PF 1022F substance from said filtrate.

Further, according to our further study, the present inventors have now found that when the cultivation of PF 1022 strain above-mentioned used as the strain capable of producing the PF 1022F substance, PF 1022G substance and PF 1022 is conducted in such a manner that the cultivation of the PF 1022 strain is carried out in a culture medium containing the ordinary carbon and nitrogen sources and in the presence of p-hydroxyphenyllactic acid or its sodium or potassium salt as added positively in an amount of 0.1~5% by weight based on the weight of the culture medium, it results in that the concentration of PF 1022H substance as produced in said culture medium can be increased as high as about 3 times or more, as compared with such a case when the cultivation of said strain is carried out in the absence of the added p-hydroxyphenyllactic acid, and it has also been found that PF 1022H substance can then be recovered from the resultant culture so formed in an improved yield. In this case, there exists a possibility of increasing the yield of PF 1022G substance, too.

According to a second aspect of this invention, therefore, there is provided a process for the preparation of PF 1022F substance, PF 1022G substance and PF 1022H substance with a highly efficient production of PF 1022H substance, which process comprises cultivating the PF 1022 strain (deposited under FERM BP-2671) as the fungal strain capable of producing PF 1022F substance, PF 1022G substance and PF 1022H substance, in a culture medium containing carbon and nitrogen sources and in the presence of p-hydroxyphenyllactic acid or sodium or potassium salt thereof as added to the culture medium in an amount of 0.1~5% based on the weight of the culture medium, at a cultivation temperature of 15~30° C., continuing the cultivation of the PF 1022 strain until the concentration of PF 1022H substance arrives at or near its maximum in the resulting culture, thereby producing and accumulating in the resulting culture PF 1022F substance, PF 1022G substance and PF 1022H substance along with PF 1022A substance, PF 1022B substance, PF 1022C substance, PF 1022D substance and PF 1022E substance, then recovering from the culture PF 1022F substance, PF 1022G substance and PF 1022H substance, and subsequently isolating PF 1022F substance, PF 1022G substance and PF 1022H substance from each other.

In the process according to the second aspect of this invention, too, the cultivation of the PF 1022 strain and the recovery of PF 1022F, G and H substances from the culture can be carried out in the same manner as in the process according to the first aspect of this invention.

In the process according to the second aspect of this invention, however, it is preferred that this process includes the steps of separating the cultured cells of PF 1022 strain from the resulting culture of the PF 1022 strain, extracting the so separated, cultured cells with methanol to obtain the methanolic solution containing PF 1022F substance, PF 1022G substance and PF 1022H substance together with PF 1022A substance, PF 1022B substance, PF 1022C substance, PF 1022D substance and PF 1022E substance, then distilling off the methanol from said methanolic solution to give a concentrated solution, stirring the concentrated solution at room temperature or lower to allow crystals comprising a mixture of PF 1022A substance, PF 1022B substance, PF 1022C substance, PF 1022D substance and PF 1022E substance as well as PF 1022G substance and PF 1022H substance to precipitate, filtering off the crystals from the mother liquor containing PF 1022F substance remaining dissolved therein, subsequently recovering PF 1022G substance and PF 1022H substance from said crystals with isolating PF 1022G substance and PF 1022H substance from each other by recrystallization and chromatographic methods in combination, and further recovering and isolating PF 1022F substance from the mother liquor remaining after the filtration of said crystals.

Further, according to a third aspect of this invention, there is provided a novel cyclic depsipeptide, which is PF 1022G substance represented by the following formula:

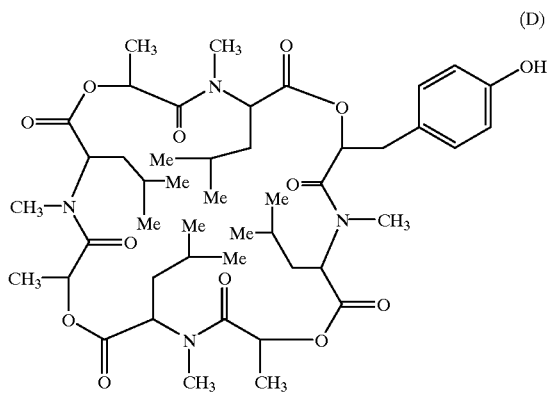

(D)

PF 1022G substance is in the form of colorless crystalline powder melting at 138.1~139.4° C. which has physico-chemical properties described in detail after the Examples 1~2 given hereinafter. PF 1022G substance possesses an anthelmintic activity against fowl roundworms.

PF 1022F, G and H substances, which are produced according to this invention, may be utilized as a starting material for the syntheses of anthelmintically active cyclic depsipeptide derivatives. For instance, PF 1022G substance and PF 1022H substance each may be utilized for the preparation of various other cyclic depsipeptide derivatives by treating the hydroxyl group on the benzyl group of PF 1022G or H substance through chemical modification or conversion with using such chemical reactions which are applicable to the normally phenolic hydroxyl group. Typically, PF 1022G substance may be used as an intermediate for the syntheses of the compounds disclosed in the specification of WO95/07272 mentioned hereinbefore, and PF 1022H substance may be used as an intermediate for the syntheses of the compounds disclosed in the specification of WO93/19053 or WO97/11064. It is particularly advantageous for industrial processes of preparing PF 1022F substance, PF 1022G substance and PF 1022H substance that all the PF 1022F, G and H substances can be produced at the same time by the fermentative processes comprising the cultivation of microorganisms according to this invention. In addition, the processes of this invention are of industrially high value in that these processes can provide by the convenient procedure PF 1022F~H substances which are useful as intermediates for synthetic production of other cyclic depsipeptide derivatives by the chemical conversion.

BEST MODE FOR CARRYING OUT THE INVENTION

Figure 1:
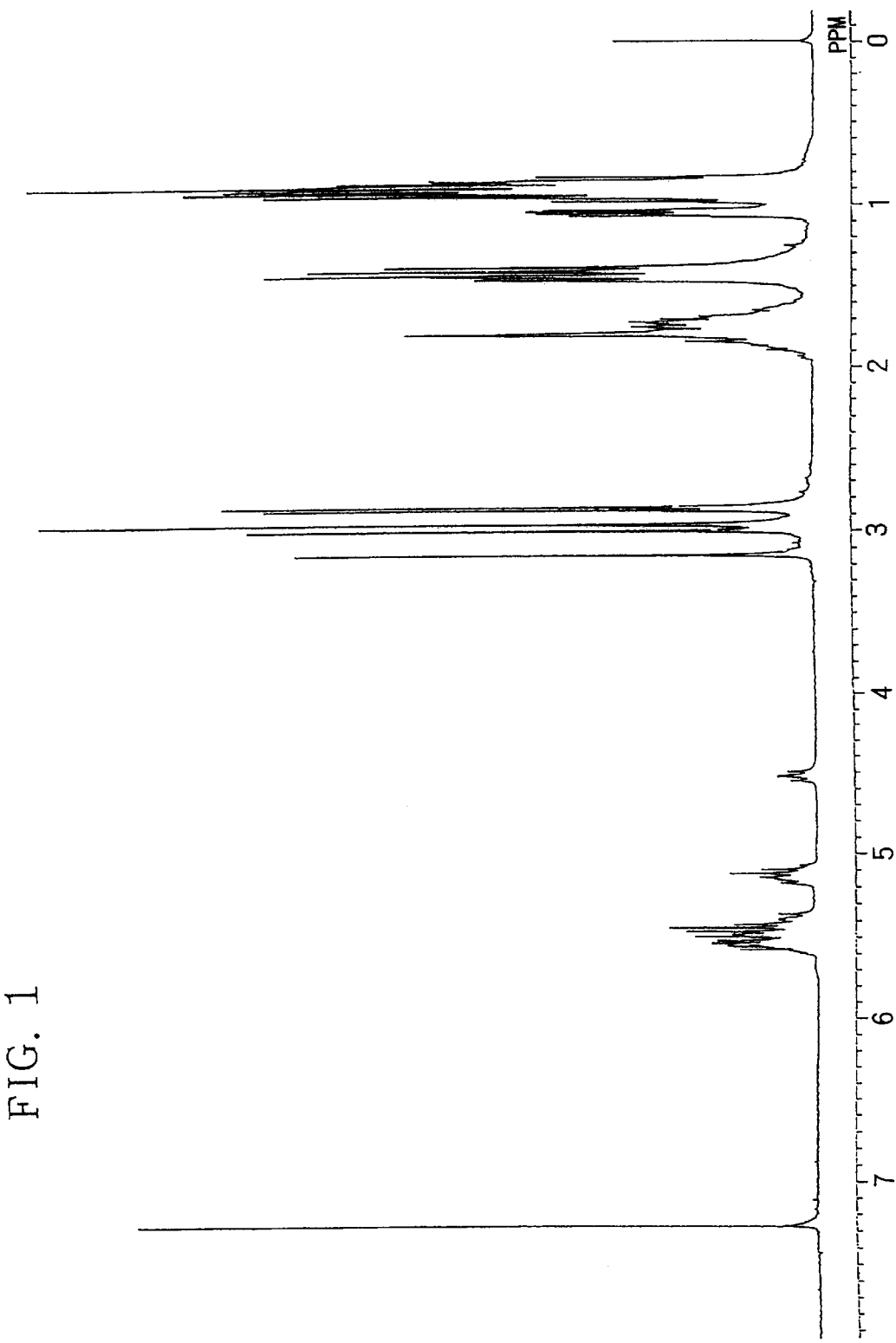
FIG. 1 shows a proton nuclear magnetic resonance spectrum of PF 1022F substance as determined in a deutero-chloroform solution at 270 MHz, where the abscissa represents chemical shift (ppm: δ).

Examples of this invention are now given. Since the properties of PF 1022F substance, PF 1022G substance and PF 1022H substance have been elucidated in this invention, the processes for the preparation of PF 1022F substance, PF 1022G substance and PF 1022H substance by the cultivation of a microorganism may be modified in a variety of ways within the scope of this invention in view of these properties of PF 1022F, G and H substances. Accordingly, this invention is not limited to the following Examples, but includes possible modifications of the Examples hereinafter given.

EXAMPLE 1

(a) A culture medium comprising 2.0% soluble starch, 1.0% glucose, 0.5% polypeptone, 0.6% wheat germ, 0.3% east extract, 0.2% soybean cake, 0.2% calcium carbonate and the balance water was used as the seed culture medium, medium comprising 2.0% glucose, 1.0% starch, 0.8% wheat germ, 1.3% soybean cake, 0.38% meat extract, 0.13% sodium chloride, 0.15% calcium carbonate and the balance water. All these media were used by adjusting the pH to 7.0 before sterilization.

The cultivation of the PF 1022 strain was effected as follows:

The seed culture medium above-mentioned was placed in 40 ml-portions into 200 ml-capacity Erlenmeyer flasks. The seed culture media in the flasks were sterilized at 120° C. for 15 minutes and then inoculated with 2~3 loopfuls of a slant culture of the PF 1022 strain (deposited under FERM BP-2671) per flask. Shake-cultivation was conducted at 26° C. for 48 hours to give a primary seed culture. Then, the seed culture medium of the same composition as above was placed in 500 ml-portions into 2 liter-capacity Erlenmeyer flasks, sterilized at 120° C. for 15 minutes and inoculated with the content of the two flasks containing said primary seed culture, followed by cultivating the PF 1022 strain under shaking at 26° C. for 48 hours. Further, the seed culture medium as above (500 liters) was charged into a 1 liter capacity-tank fermenter, sterilized at 120° C. for 25 minutes and then inoculated with the content of the five flasks containing the said primary seed culture and subsequently cultivated under stirring at 26° C. for 48 hours to give a tank seed culture.

Then, the production culture medium as above (5 kilo-liters) was charged into a 10 kilo-liter capacity-tank fermenter and sterilized at 120° C. for 25 minutes. The production culture medium so sterilized was inoculated with 0.5 kilo-liters of the tank seed culture obtained in the above and then cultivated at 26° C. for 7 days with aeration and under stirring. After the completion of the cultivation, the culture broth so obtained was filtered with the addition of diatomaceous earth as a filtering aid, to yield the cultured cells of the PF 1022 strain (about 2700 kg).

(b) The recovery of PF 1022F~H substances from the cultured cells were carried out as follows:

Thus, methanol (14.4 kilo-liters) was added to the cultured cells obtained as above (about 2700 kg), and the resultant mixture was stirred for 3 hours. Thereafter, the cells were filtered off to yield the methanolic extract from the cells. The methanol was distilled off from the methanolic extract under a reduced pressure to give a concentrated solution (960 liters). The concentrated solution was stirred at room temperature for a whole day and one night, and the resulting crystals (primary crystals) as deposited were collected by filtration.

The primary crystals (about 60 kg) so obtained comprised a mixture of PF 1022A substance, PF 1022B substance, PF 1022C substance, PF 1022D substance, PF 1022E substance, PF 1022F substance, PF 1022G substance, PF 1022H substance and other cell constituents. The filtrate also contained the above-mentioned PF 1022A substance, PF 1022B substance, PF 1022C substance, PF 1022D substance, PF 1022E substance, PF 1022F substance, PF 1022G substance, PF 1022H substance and other cell constituents, but the proportions of these constituents present in the filtrate were different from those of the primary crystals, while the proportion of PF 1022F substance is relatively higher in the filtrate. The primary mother liquor obtained was stored and used later for the recovery of PF 1022F substance therefrom.

The primary crystals as above were washed twice with n-heptane (200 liters). The crystals left after the washing were dissolved in methanol (500 liters), to which solution was added activated carbon (12 kg). The resultant mixture was stirred for 1 hour. After the filtration, the resulting filtrate was concentrated under reduced pressure to a volume of 170 liters. The concentrated solution so obtained was stirred at room temperature for 24 hours, and the crystals so precipitated (the secondary crystals) were collected by filtration.

The secondary crystals (about 35 kg) comprised a mixture of the PF 1022A substance as a main constituent along with PF 1022C substance, PF 1022D substance, PF 1022E substance and PF 1022G substance.

The secondary crystals were washed twice with n-heptane (each 240 liters), then dissolved in methanol (350 liters) and then the methonolic solution was concentrated under a reduced pressure to a volume of 100 liters. The concentrated solution obtained was stirred at room temperature for 24 hours and the crystals thus obtained (the tertiary crystals) was collected by filtration.

The tertiary crystals so obtained (about 31 kg) contained PF 1022A substance in a high purity.

(c) The filtrate (the mother liquor) which remained at the filtration out of the secondary crystals above was containing PF 1022A, B, C, D, E, F, G and H substances. On the other hand, the filtrate (the mother liquor) remaining at the filtration out of the tertiary crystals above was containing PF 1022A, C, D, E and G substances. These two filtrates were combined and concentrated under a reduced pressure up to a volume of 65 liters. The crystals so precipitated were washed twice with n-heptane (25 liters and 23 liters, respectively) and then dried under reduced pressure, to afford crystals (8.2 kg).

The crystals so obtained comprised a mixture of the PF 1022A substance, PF 1022B substance, PF 1022C substance, PF 1022D substance, PF 1022E substance, PF 1022G substance and PF 1022H substance. A half amount (4.1 kg) of the crystals so obtained was dissolved in chloroform (10 liters) and the resulting chloroform solution was subjected to a silica gel column chromatography ( Wako gel C-300, 20 kg). The silica gel column was first eluted with a developing solvent (380 liters) consisting of chloroform-ethyl acetate (6:1) and then eluted with a developing solvent (140 liters) consisting of chloroform-ethyl acetate (1:1). The resulting eluate was collected in 50-liter-fractions. Fractions Nos.8~10 of the eluate contained PF 1022E substance, PF 1022G substance and PF 1022H substance as main constituents and were combined together and then concentrated under reduced pressure.

The powder thus obtained (158 g) comprised a mixture of PF 1022E substance, PF 1022G substance and PF 1022H substance. The powder (158 g) was crystallized from ethyl acetate (800 ml) and the crystals was collected by filtration. A portion (2.5 g) of the crystals so obtained (121.6 g) was dissolved in toluene (10 ml), and the solution in toluene was subjected to a silica gel column chromatography (Wako gel C-200, 100 g). The elution was effected with a developing solvent consisting of ethyl acetate-n-hexane (1:1), and the eluate was collected in 20 ml-fractions. Fractions Nos.38~42 of the eluate were combined and concentrated to dryness under a reduced pressure, affording the PF 1022G substance (34.7 mg). Fractions Nos.44~48 of the eluate were combined and concentrated to dryness under a reduced pressure, affording the PF 1022H substance (26.5 mg).

(d) On the other hand, the stored filtrate (the mother liquor of the primary crystals) remaining from the filtering operation of the primary crystals above was concentrated to dryness under a reduced pressure to give a powder. A portion (2.35 kg) of said powder was dissolved in chloroform (10 liters) and the resultant solution was subjected to a silica gel column chromatography (Wako gel C-300, 20 kg). The silica gel column was first eluted with a developing solvent (420 liters) consisting of chloroform-ethyl acetate (6:1), and then eluted with a developing solvent (120 liters) consisting of chloroform-ethyl acetate (1:1). The eluates were collected in 50 liter-fractions. Fraction No.10 of the eluate contained PF 1022E substance, PF 1022F substance, PF 1022G substance and other substances so eluted, and the fraction No.10 was concentrated under a reduced pressure.

The powder (45.0 g) so obtained was subjected to a silica gel column chromatography (Wako gel C-300, 550 g). Elution was effected with a developing solvent (4 liters) consisting of chloroform-ethyl acetate (3:1) and the eluate was collected in 500 ml-fractions. Fractions Nos.3~7 containing the PF 1022F substance were combined and then concentrated under reduced pressure, to afford a powder (9.19 g) comprising PF 1022E substance, PF 1022F substance and other substances.

This powder was dissolved in a 60% aqueous acetonitrile, and the resulting solution was subjected to a reversed phase column chromatography (Cosmosil 75C18OPN, 100 g). The elution was effected first with a 60% aqueous acetonitrile (500 ml), then with a 70% aqueous acetonitrile (400 ml) and finally with an 80% aqueous acetonitrile (900 ml). The eluates obtained were collected in 200 ml-fractions. Eluate fractions Nos.2~8 containing PF 1022F substance were combined and then concentrated under reduced pressure, to afford a crude powder (6.53 g) of PF 1022F substance.

This crude powder was dissolved in toluene (30 ml) and the solution obtained was subjected to a silica gel column chromatography (Wako gel C-200, 260 g). Elution was effected first with a developing solvent (1 liter) consisting of n-hexane-ethyl acetate (55:45), then with a developing solvent (2 liters) consisting of n-hexane-ethyl acetate (1:1), and finally with a developing solvent (1 liter) consisting of n-hexane-ethyl acetate (45:55). The eluates were collected in 200 ml-fractions. Eluate fractions Nos.20~21 containing PF 1022F substance only were combined and then concentrated under a reduced pressure, to afford PF 1022F substance (143 mg).

EXAMPLE 2

(a) The seed culture medium (50 ml) having the same composition as described in Example 1 above was placed into each of 250 ml-Erlenmeyer flasks. The flasks, after sterilizing at 120° C. for 15 minutes, were inoculated with 2~3 loopfuls of a slant culture of the PF 1022 strain and then incubated at 26° C. for 3 days. The resulting culture broth was separated into two portions. To one portion of said two portions was added p-hydroxyphenyllactic acid in an amount of 0.3% by weight based on the weight of the culture medium present in said one portion. Both the two portions were separately further incubated at 26° C. for 3 days. The resulting cultured cells obtained from the incubated two portions of the culture broth were extracted with methanol in a manner similar to the procedure disclosed in Example 1(b). The concentration (μg/ml) of PF 1022H substance in the resulting two methanolic extracts was assayed by a liquid column chromatography (column: a product of GL Science Co., Inertsil ODS-2: 4.6 mmφ×250 mm; at temperature of 40° C.; flow rate of 1 ml/min.; detecting UV at 210 nm, mobile phase consisting of 80% acetonitrile+0.1% trifluoroacetic acid; at retention time of 5.0 minutes). Then, comparison was made to estimate the difference in the quantity of production of PF 1022H substance in the resulting methanolic extracts of the cultured cells between the case when the cultured cells were obtained from the incubation of the PF 1022 strain in the presence of p-hydroxyphenyllactic acid added, and the case when the cultured cells were obtained from the incubation of the PF 1022 strain in the absence of p-hydroxylphenyllactic acid. As a result, it was found that the concentration of PF 1022H substance in the methanolic extract of the cultured cells as in the presence of p-hydroxyphenyllactic acid added was 132 μg/ml, whereas the concentration of PF 1022H substance in the methanolic extract of the cultured cells as incubated without the addition of p-hydroxyphenyllactic acid was 35 μg/ml.

(b) The seed culture medium (50 ml) having the same composition as described in Example 1(a) was placed into each of one hundred of 250 ml-Erlenmeyer flasks. The culture medium in the one hundred (100) of the flasks above were sterilized at 120° C. for 15 minutes. Thereafter, the seed culture medium of each of the 100 flasks (total volume of the seed medium: 5 liters) was inoculated with 2~3 loopfuls of the PF 1022 strain (deposited under FERM BP-2671) and then incubated at 26° C. for 3 days.

Then, p-hydroxyphenyllactic acid was added to the resulting culture in each flask so that said acid was present in an amount of 0.3% by weight based on the weight of the culture medium present in each flask. The cultivation of the PF 1022 strain was then continued at 26° C. for further 3 days under aeration and stirring. After the completion of the cultivation, the resulting culture broth was filtered with aid of diatomaceous earth as a filtering aid, thus to obtain the cultured cells of the PF 1022 strain (about 2.5 kg).

(c) The cultured cells (2.5 kg), so obtained were added with methanol (13 liters) and then were stirred for 3 hours. Thereafter, the cells were filtered off to give a methanolic extract from the cultured cells. The methanol was distilled off from the methanolic extract to yield a concentrated solution (870 ml). The concentrated solution was stirred at room temperature for 24 hours, when the primary crystals were precipitated. The primary crystals were collected by filtration and the crystals (55 g) so obtained were washed with n-heptane and then again dissolved in methanol (450 ml). The resulting methanolic solution was treated in the manner similar to Example 1(b), i.e. by a treatment with an activated carbon followed by concentration and crystallization treatment. Thus, there were obtained secondary crystals (32 g), as well as a filtrate (the mother liquor of the secondary crystals) obtained by the filtration of the secondary crystals. The resultant secondary crystals were again dissolved in methanol (320 ml) as in Example 1(b), and the methanolic solution so obtained was again treated by concentration and crystallization, thus to yield tertiary crystals (28 g), as well as a filtrate (the mother liquor of the tertiary crystals) obtained by the filtration of the tertiary crystals.

(d) The mother liquor of the secondary crystals and the mother liquor of the tertiary crystals obtained as above were combined and then concentrated to a volume of 60 ml. The resulting crystals were washed twice with n-heptane and then dried under reduced pressure, to yield crystals (7.5 g).

The crystals obtained above were dissolved in chloroform and the resulting chloroform solution was subjected to a silica gel column chromatography in the manner similar to Example 1(c). Eluate fractions containing the PF 1022E substance, PF 1022G substance and PF 1022H substance thus eluted were collected and then concentrated under reduced pressure, to give a crude powder comprising PF 1022E substance, PF 1022G substance and PF 1022H substance, which was then recrystallized from ethyl acetate.

The crystals so recrystallized were again dissolved in toluene and the resulting toluene solution was subjected to a silica gel column chromatography (developed with ethyl acetate-n-hexane, 1:1) in the same manner as in Example 1(c), thus to afford the eluate fractions containing PF 1022G substance and also the eluate fractions containing PF 1022H substance.

The fractions containing PF 1022G substance and the fractions containing PF 1022H substance were separately concentrated to dryness under reduced pressure, to afford PF 1022G substance (11.5 mg) and PF 1022H substance (8.8 mg), respectively.

Figure 2:
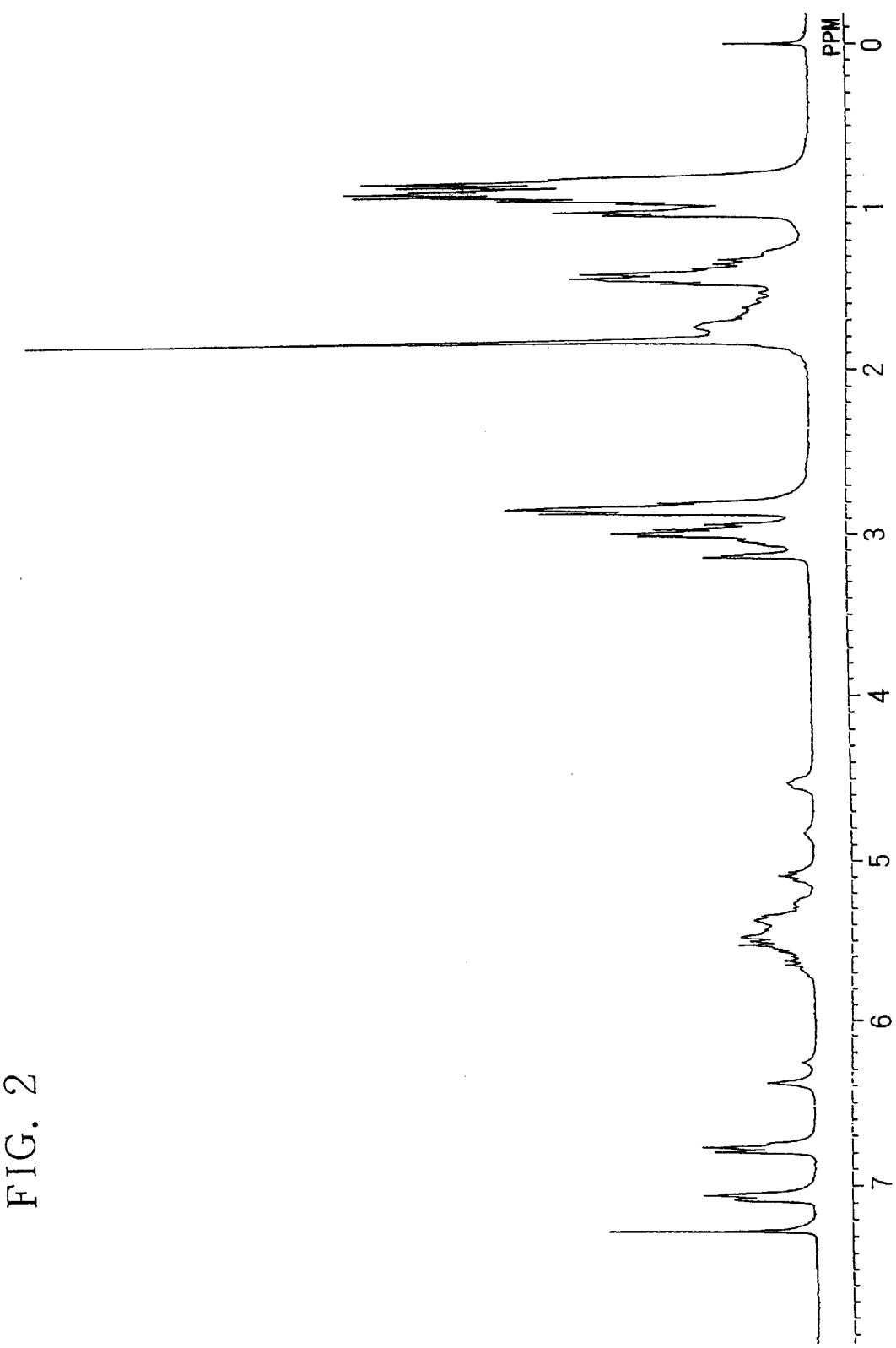
FIG. 2 shows a proton nuclear magnetic resonance spectrum of PF 1022G substance as determined in a deutero-chloroform solution at 270 MHz, where the abscissa represents chemical shift (ppm: δ).

Physico-chemical properties of PF 1022G substance, PF 1022F substance and PF 1022H substance thus obtained are given below:

(i) Physico-Chemical Properties of PF 1022F Substance
  (1) Color and appearance: Colorless needle-like crystals;
  (2) Melting point: 168~170° C.;
  (3) Molecular formula: $C_{40}H_{68}N_4O_{12}$;
  (4) Mass spectrum (FAB-MS): m/z 797 (M+H)$^+$;
  (5) Specific rotation: $[\alpha]_D^{25}$ −68° (c 0.15, methanol);
  (6) Ultraviolet absorption spectrum (in a methanolic solution):

$\lambda_{max}$ nm ($E_{1cm}^{1\%}$) 262 (3.6);

(7) Infrared absorption spectrum (IR-Card):
  ν (cm$^{-1}$) 2957, 2361, 1744, 1663, 1468, 1414, 1281, 1202, 1152, 1080, 1030, 583;
  (8) $^1$H-Nuclear magnetic resonance spectrum: (δ: ppm)
  In FIG. 1 is shown $^1$H-nuclear magnetic resonance spectrum of PF 1022F substance as determined in deuterochloroform at 270 MHz using TMS (tetramethylsilane) as internal standard.
  (9) Solubilities: Soluble in chloroform, acetone, ethyl acetate, methanol and dimethylsulfoxide; Insoluble in water and n-hexane;
  (10) Rf value on silica gel thin layer chromatography (TLC):
    Rf value is 0.34, when use is made of an eluent of chloroform-ethyl acetate (1:2) on silica gel plate 60F254 (thickness 0.25 mm, a product of Merck & Co.).
  (11) Classification by basicity, acidity or neutrality: Neutral substance;
(ii) Physico-Chemical Properties of PF 1022G Substance
  (1) Color and appearance: Colorless crystalline powder;
  (2) Melting point: 138.1~139.4° C.;
  (3) Molecular formula: $C_{46}H_{72}N_4O_{13}$;
  (4) Mass spectrum (FAB-MS): m/z 889 (M+H)$^+$; (5) Specific rotation: $[\alpha]_D^{25}$ −76° (c 0.10, methanol);

(6) Ultraviolet absorption spectrum (in a methanolic solution):

$\lambda_{max}\,nm\,(E^{1\%}_{1cm})\ 278\,(6.3);$ (7) Infrared absorption spectrum (in KBr pellet):
ν (cm$^{-1}$) 3424, 2959, 2872, 2363, 2342, 1744, 1665, 1518, 1468, 1416, 1372, 1327, 1271, 1198, 1127, 1080, 1030, 833, 507, 422;

(8) $^1$H-Nuclear magnetic resonance spectrum: (δ: ppm)
In FIG. 2 is shown $^1$H-nuclear magnetic resonance spectrum of PF 1022G substance as determined in deutero-chloroform at 270 MHz using TMS (tetramethylsilane) as internal standard.

(9) Solubilities: Soluble in chloroform, acetone, ethyl acetate, methanol and dimethylsulfoxide; Insoluble in water and n-hexane;

(10) Rf value on silica gel thin layer chromatography (TLC):
Rf value is 0.32, when use is made of an eluent of chloroform-ethyl acetate (1:2) on silica gel plate 60F254 (thickness 0.25 mm, a product of Merck & Co.).

Figure 3:
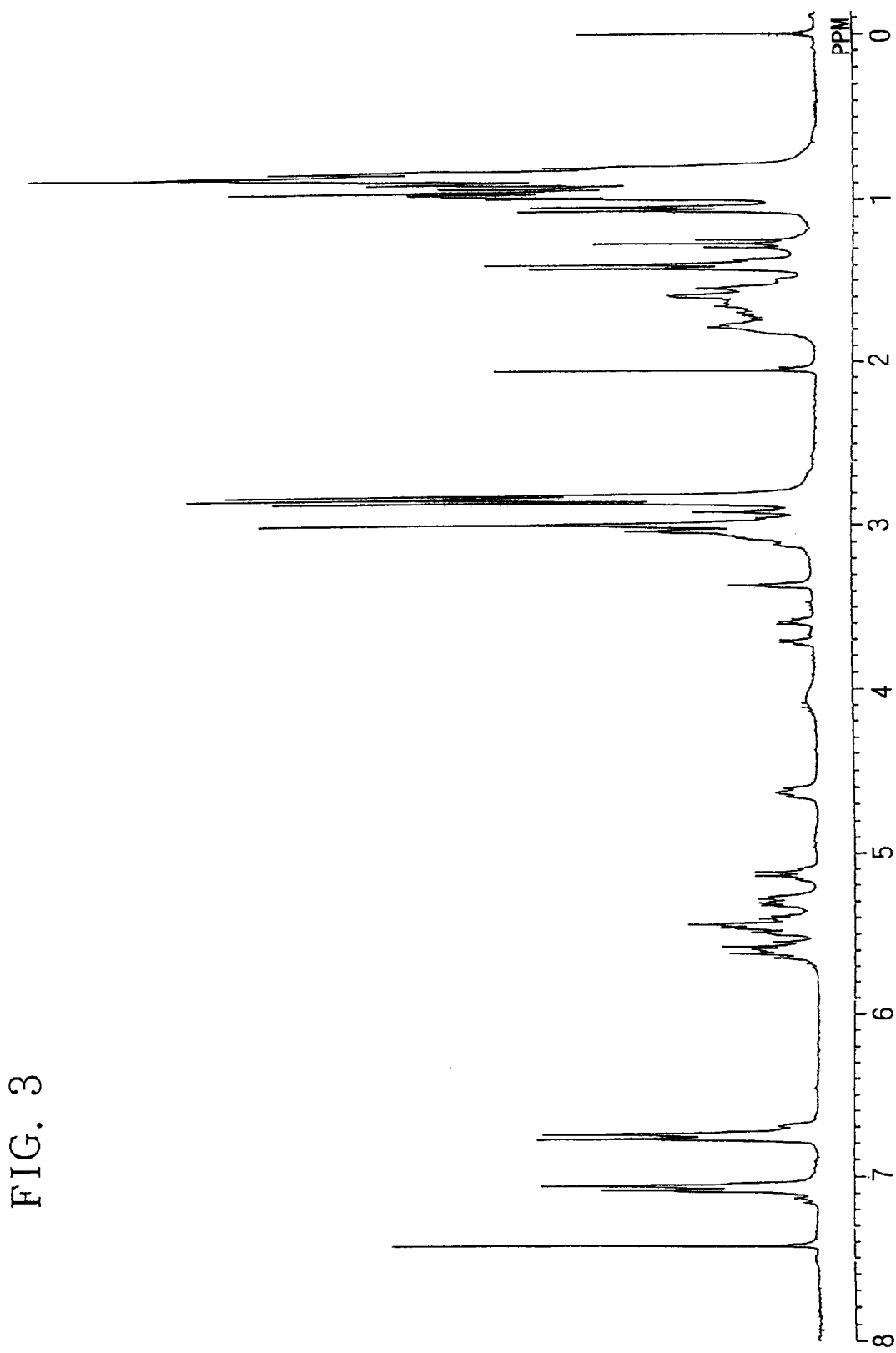
FIG. 3 shows a proton nuclear magnetic resonance spectrum of PF 1022H substance as determined in a mixed solution of deutero-chloroform-deutero-methanol at 270 MHz, where the abscissa represents chemical shift (ppm: δ).

(11) Classification by basicity, acidity or neutrality: Neutral substance;

(iii) Physico-Chemical Properties of the PF 1022H Substance (1) Color and appearance: Colorless crystalline powder;
(2) Melting point: 224.2~225.4° C.;
(3) Molecular formula: C$_{52}$H$_{76}$N$_4$O$_{14}$;
(4) Mass spectrum (FAB-MS): m/z 981 (M+H)$^+$;
(5) Specific rotation: [α]$_D^{25}$ −97° (c 0.1, methanol);
(6) Ultraviolet absorption spectrum (in a methanolic solution):

$\lambda_{max}\,nm\,(E^{1\%}_{1cm})\ 278\,(6.3);$ (7) Infrared absorption spectrum (IR-Card):
ν (cm$^{-1}$) 2959, 2363, 1744, 1657, 1518, 1468, 1273, 1209, 1155, 478, (8) $^1$H-Nuclear magnetic resonance spectrum: (δ: ppm)
In FIG. 3 is shown $^1$H-nuclear magnetic resonance spectrum of PF 1022H substance as determined in a mixed solvent of deutero-chloroform-deutero-methanol at 270 MHz using TMS (tetramethylsilane) as internal standard.

(9) Solubilities: Soluble in chloroform, acetone, ethyl acetate, methanol and dimethylsulfoxide; Insoluble in water and n-hexane;

(10) Rf value on silica gel thin layer chromatography (TLC):
Rf value is 0.25, when use is made of an eluent of chloroform-ethyl acetate (1:2) on silica gel plate 60F254 (thickness 0.25 mm, a product of Merck & Co.).

(11) Classification by basicity, acidity or neutrality: Neutral substance;

INDUSTRIAL APPLICABILITY

As explained above, the PF 1022F substance and PF 1022H substance, as well as a novel cyclic depsipeptide, PF 1022G substance, have now been produced in a convenient way by the processes according to this invention, which comprise cultivating a fungal strain capable of producing PF 1022F substance, PF 1022G substance and PF 1022H substance, which strain belongs to the genus Xylaria or the genus Rosellinia in the family Xylariaceae.

The PF 1022F substance, PF 1022G substance and PF 1022H substance thus produced are the cyclic depsipeptides having anthelmintic activities and also are useful as starting materials to be used for the chemical syntheses of such known or novel derivatives of PF 1022 substance which have higher anthelmintic activities.

What is claimed is:
1. A cyclic depsipeptide, which is PF 1022G substance represented by the following formula:

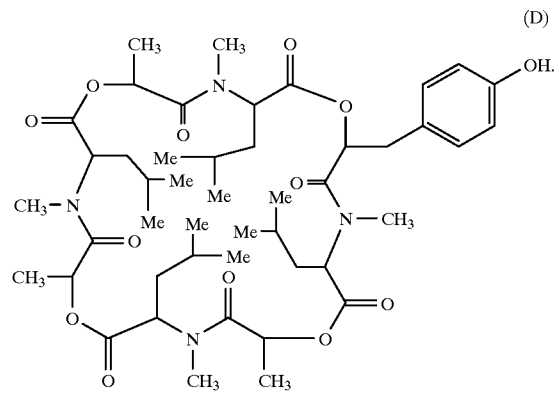

(D)

* * * * *